(12) United States Patent
Robertson et al.

(10) Patent No.: US 10,990,165 B2
(45) Date of Patent: *Apr. 27, 2021

(54) MEDICAL DEVICE USAGE MONITORING SYSTEM AND METHOD

(71) Applicants: Hadley Allen Robertson, Fort Lauderdale, FL (US); Delaney Lee Robertson, Fort Lauderdale, FL (US)

(72) Inventors: Hadley Allen Robertson, Fort Lauderdale, FL (US); Delaney Lee Robertson, Fort Lauderdale, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/925,673

(22) Filed: Jul. 10, 2020

(65) Prior Publication Data
US 2021/0011544 A1 Jan. 14, 2021

Related U.S. Application Data

(60) Provisional application No. 62/873,541, filed on Jul. 12, 2019.

(51) Int. Cl.
*G06F 3/01* (2006.01)
*G16H 40/67* (2018.01)
(Continued)

(52) U.S. Cl.
CPC ............ *G06F 3/011* (2013.01); *A61B 5/1126* (2013.01); *A61B 5/4833* (2013.01); *A61B 5/742* (2013.01);
(Continued)

(58) Field of Classification Search
CPC . A61B 5/0205; A61B 5/02416; A61B 5/1112; A61B 5/1118; A61B 5/1123;
(Continued)

(56) References Cited

U.S. PATENT DOCUMENTS 6,514,200 B1 2/2003 Khouri
6,890,285 B2* 5/2005 Rahman ............... A61B 5/4833
482/4

(Continued)

OTHER PUBLICATIONS

International Search Report and Written Opinion issued in related International Application Serial No. PCT/US2020/041521 dated Sep. 14, 2020, 11 pages.

(Continued)

*Primary Examiner* — Stephen R Burgdorf
(74) *Attorney, Agent, or Firm* — Michael T. Abramson; Holland & Knight LLP

(57) ABSTRACT

A method, computer program product, and computer system for receiving, by a computing device, a total amount of time that a user wears a wearable device during one or more time periods. The total amount of time that the user wears the wearable device during the one or more time periods may be compared to a threshold amount of time for the one or more time periods. A remaining amount of time for the user to wear the wearable device during the one or more time periods may be displayed on a user interface based upon, at least in part, comparing the total amount of time that the user wears the wearable device during the one or more time periods to the threshold amount of time.

15 Claims, 8 Drawing Sheets

(51) Int. Cl.
*G16H 15/00* (2018.01)
*A61B 5/00* (2006.01)
*G04F 10/00* (2006.01)
*A61B 5/11* (2006.01)
*A61F 5/02* (2006.01)
*G16H 20/30* (2018.01)

(52) U.S. Cl.
CPC ............. *G04F 10/00* (2013.01); *G16H 15/00* (2018.01); *G16H 40/67* (2018.01); *A61B 2562/0247* (2013.01); *A61B 2562/0271* (2013.01); *A61F 5/02* (2013.01); *G16H 20/30* (2018.01)

(58) Field of Classification Search
CPC ... A61B 5/1126; A61B 5/4812; A61B 5/4833; A61B 5/681; A61B 5/742; A61B 2562/0247; A61B 2562/0271; A61F 5/02; A63B 24/0006; A63B 24/0062; G04F 10/00; G06F 3/011; G06F 8/65; G06F 9/46; G06F 19/3481; G06N 20/00; G06N 99/005; G08B 21/0415; G08C 17/00; G09B 19/00; G09B 19/0038; G16H 15/00; G16H 20/30; G16H 40/67
See application file for complete search history.

(56) References Cited

U.S. PATENT DOCUMENTS

| | | | |
|---|---|---|---|
| 8,753,275 B2 | 6/2014 | Najafi et al. | |
| 10,470,847 B2 | 11/2019 | Shanjani et al. | |
| 2002/0022973 A1 | 2/2002 | Sun et al. | |
| 2005/0171410 A1* | 8/2005 | Hjelt ...................... | G16H 40/67 600/300 |
| 2006/0166157 A1 | 7/2006 | Rahman et al. | |
| 2009/0024062 A1 | 1/2009 | Einarsson | |
| 2012/0184878 A1 | 7/2012 | Najafi et al. | |
| 2013/0142367 A1* | 6/2013 | Berry ..................... | G16H 40/40 381/315 |
| 2013/0150755 A1* | 6/2013 | Kubiak .................... | A61B 5/11 600/592 |
| 2013/0345612 A1 | 12/2013 | Bannister et al. | |
| 2014/0127729 A1 | 5/2014 | Moran et al. | |
| 2014/0257156 A1* | 9/2014 | Capra .................. | A43C 11/165 602/5 |
| 2016/0007934 A1* | 1/2016 | Arnold ................. | A61B 5/4809 600/595 |
| 2016/0026212 A1* | 1/2016 | Lee ....................... | G06F 1/3231 361/679.03 |
| 2016/0041048 A1 | 2/2016 | Blum et al. | |
| 2016/0262687 A1 | 9/2016 | Vaidyanathan et al. | |
| 2016/0317083 A1* | 11/2016 | DeLuke ................. | A61F 5/3738 |
| 2016/0324681 A1 | 11/2016 | Flanagan | |
| 2016/0364131 A1* | 12/2016 | Dumont ................. | G16H 40/63 |
| 2017/0000386 A1* | 1/2017 | Salamatian .......... | A61B 5/6802 |
| 2017/0156639 A1 | 6/2017 | Gokhale et al. | |
| 2017/0319381 A1* | 11/2017 | Rogers .................... | A61F 7/12 |
| 2018/0015284 A1 | 1/2018 | Coleman et al. | |
| 2018/0055660 A1* | 3/2018 | Macmahon ........... | A61B 5/4561 |
| 2020/0174517 A1 | 6/2020 | Martinez et al. | |
| 2020/0405230 A1* | 12/2020 | Svanegaard ........... | A61B 5/742 |

OTHER PUBLICATIONS

International Search Report and Written Opinion issued in related International Application Serial No. PCT/US2020/041526 dated Sep. 14, 2020, 16 pages.
Non-Final Office Action issued in related U.S. Appl. No. 16/925,652 dated Sep. 15, 2020, 17 pages.
Final Office Action issued in related U.S. Appl. No. 16/925,652 dated Dec. 16, 2020, 24 pages.
Notice of Allowance issued in related U.S. Appl. No. 16/925,652 dated Feb. 4, 2021; 24 pages.

\* cited by examiner

MEDICAL DEVICE USAGE MONITORING SYSTEM AND METHOD

RELATED CASES

This application claims the benefit of U.S. Provisional Application No. 62/873,541, filed on 12 Jul. 2019, the contents of which are all incorporated by reference.

BACKGROUND

Generally, after a patient is diagnosed with a back problem (e.g., idiopathic scoliosis), a doctor or other health processional may prescribe a back brace. In order for it to significantly improve the position of the spine, guidelines say the brace has to be worn a certain number of hours per day based on the patient's spinal curvature (commonly up to or exceeding eighteen hours a day). Patients must adhere to these guidelines to reap the full benefits of the back brace.

BRIEF SUMMARY OF DISCLOSURE

In one example implementation, a method, performed by one or more computing devices, may include but is not limited to receiving, by a computing device, a total amount of time that a user wears a wearable device during one or more time periods. The total amount of time that the user wears the wearable device during the one or more time periods may be compared to a threshold amount of time for the one or more time periods. A remaining amount of time for the user to wear the wearable device during the one or more time periods may be displayed on a user interface based upon, at least in part, comparing the total amount of time that the user wears the wearable device during the one or more time periods to the threshold amount of time.

One or more of the following example features may be included. The total amount of time that the user wears the wearable device during the one or more time periods may be received manually. The total amount of time that the user wears the wearable device during the one or more time periods may be received automatically. The total amount of time that the user wears the wearable device during the one or more time periods may be received by a sensor connected to the wearable device, wherein the sensor may include at least one of a capacitive sensor, a proximity sensor, a pressure sensor, a temperature sensor, and a motion sensor. Displaying on the user interface the remaining amount of time for the user to wear the wearable device during the one or more time periods may include displaying a surplus amount of time above the threshold amount of time that the user wears the wearable device during the one or more time periods. Displaying on the user interface the remaining amount of time for the user to wear the wearable device during the one or more time periods may include applying the surplus amount of time above the threshold amount of time to the remaining amount of time for the user to wear the wearable device during the one or more time periods. The wearable device may include at least one of a back brace, a knee brace, an ankle brace, a sling, a removable cast, a posture device, and a post-surgical stabilization device.

In another example implementation, a computing system may include one or more processors and one or more memories configured to perform operations that may include but are not limited to receiving a total amount of time that a user wears a wearable device during one or more time periods. The total amount of time that the user wears the wearable device during the one or more time periods may be compared to a threshold amount of time for the one or more time periods. A remaining amount of time for the user to wear the wearable device during the one or more time periods may be displayed on a user interface based upon, at least in part, comparing the total amount of time that the user wears the wearable device during the one or more time periods to the threshold amount of time.

One or more of the following example features may be included. The total amount of time that the user wears the wearable device during the one or more time periods may be received manually. The total amount of time that the user wears the wearable device during the one or more time periods may be received automatically. The total amount of time that the user wears the wearable device during the one or more time periods may be received by a sensor connected to the wearable device, wherein the sensor may include at least one of a capacitive sensor, a proximity sensor, a pressure sensor, a temperature sensor, and a motion sensor. Displaying on the user interface the remaining amount of time for the user to wear the wearable device during the one or more time periods may include displaying a surplus amount of time above the threshold amount of time that the user wears the wearable device during the one or more time periods. Displaying on the user interface the remaining amount of time for the user to wear the wearable device during the one or more time periods may include applying the surplus amount of time above the threshold amount of time to the remaining amount of time for the user to wear the wearable device during the one or more time periods. The wearable device may include at least one of a back brace, a knee brace, an ankle brace, a sling, a removable cast, a posture device, and a post-surgical stabilization device.

In another example implementation, a computer program product may reside on a computer readable storage medium having a plurality of instructions stored thereon which, when executed across one or more processors, may cause at least a portion of the one or more processors to perform operations that may include but are not limited to receiving a total amount of time that a user wears a wearable device during one or more time periods. The total amount of time that the user wears the wearable device during the one or more time periods may be compared to a threshold amount of time for the one or more time periods. A remaining amount of time for the user to wear the wearable device during the one or more time periods may be displayed on a user interface based upon, at least in part, comparing the total amount of time that the user wears the wearable device during the one or more time periods to the threshold amount of time.

One or more of the following example features may be included. The total amount of time that the user wears the wearable device during the one or more time periods may be received manually. The total amount of time that the user wears the wearable device during the one or more time periods may be received automatically. The total amount of time that the user wears the wearable device during the one or more time periods may be received by a sensor connected to the wearable device, wherein the sensor may include at least one of a capacitive sensor, a proximity sensor, a pressure sensor, a temperature sensor, and a motion sensor. Displaying on the user interface the remaining amount of time for the user to wear the wearable device during the one or more time periods may include displaying a surplus amount of time above the threshold amount of time that the user wears the wearable device during the one or more time periods. Displaying on the user interface the remaining amount of time for the user to wear the wearable device during the one or more time periods may include applying the surplus amount of time above the threshold amount of time to the remaining amount of time for the user to wear the wearable device during the one or more time periods. The wearable device may include at least one of a back brace, a knee brace, an ankle brace, a sling, a removable cast, a posture device, and a post-surgical stabilization device.

The details of one or more example implementations are set forth in the accompanying drawings and the description below. Other possible example features and/or possible example advantages will become apparent from the description, the drawings, and the claims. Some implementations may not have those possible example features and/or possible example advantages, and such possible example features and/or possible example advantages may not necessarily be required of some implementations.

BRIEF DESCRIPTION OF THE DRAWINGS

Like reference symbols in the various drawings may indicate like elements.

DETAILED DESCRIPTION

Figure 1:
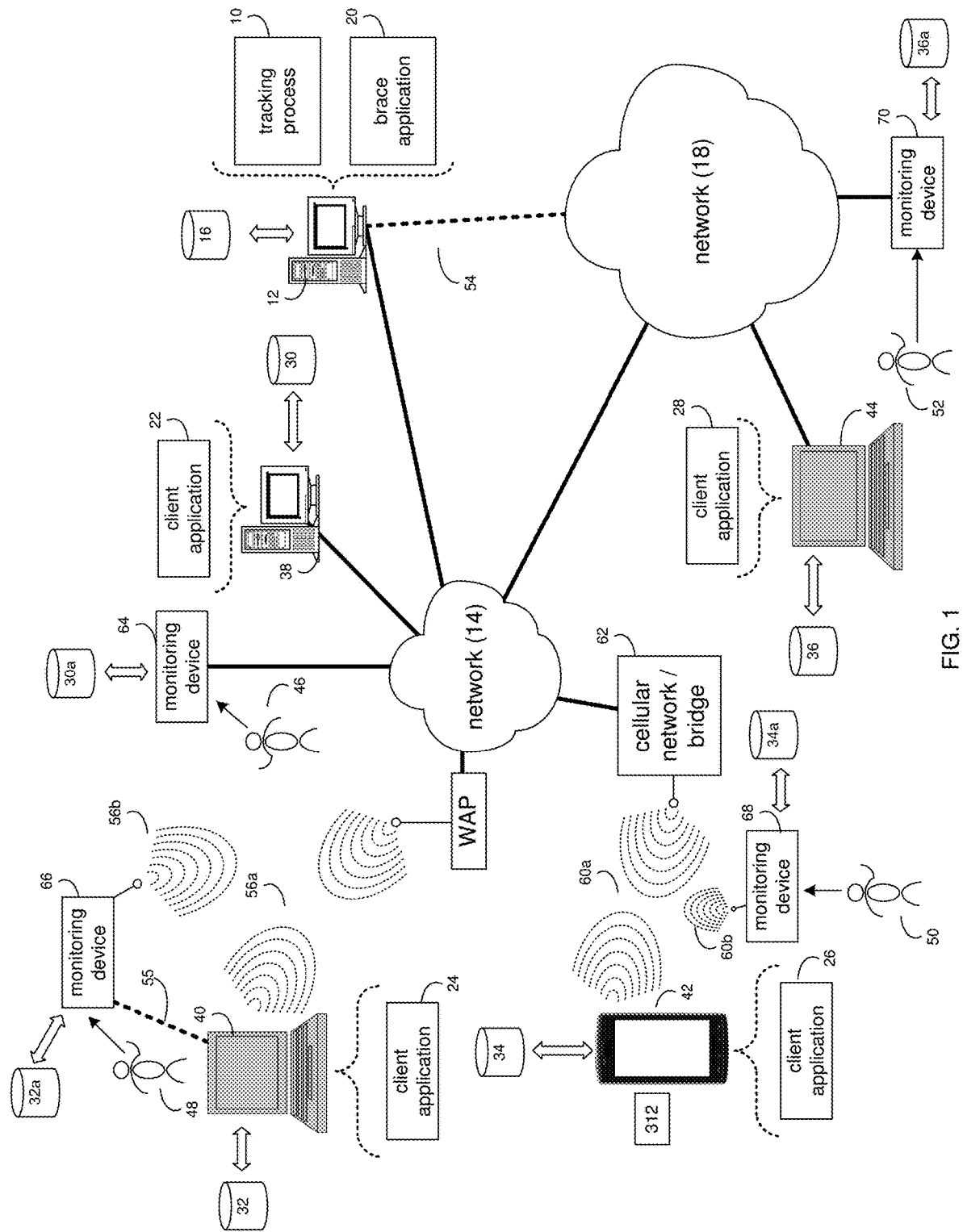
FIG. 1 is an example diagrammatic view of a tracking process coupled to an example distributed computing network according to one or more example implementations of the disclosure.

System Overview:

In some implementations, the present disclosure may be embodied as a method, system, or computer program product. Accordingly, in some implementations, the present disclosure may take the form of an entirely hardware implementation, an entirely software implementation (including firmware, resident software, micro-code, etc.) or an implementation combining software and hardware aspects that may all generally be referred to herein as a "circuit," "module" or "system." Furthermore, in some implementations, the present disclosure may take the form of a computer program product on a computer-usable storage medium having computer-usable program code embodied in the medium.

In some implementations, any suitable computer usable or computer readable medium (or media) may be utilized. The computer readable medium may be a computer readable signal medium or a computer readable storage medium. The computer-usable, or computer-readable, storage medium (including a storage device associated with a computing device or client electronic device) may be, for example, but is not limited to, an electronic, magnetic, optical, electromagnetic, infrared, or semiconductor system, apparatus, device, or any suitable combination of the foregoing. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a digital versatile disk (DVD), a static random access memory (SRAM), a memory stick, a floppy disk, a mechanically encoded device such as punch-cards or raised structures in a groove having instructions recorded thereon, a media such as those supporting the internet or an intranet, or a magnetic storage device. Note that the computer-usable or computer-readable medium could even be a suitable medium upon which the program is stored, scanned, compiled, interpreted, or otherwise processed in a suitable manner, if necessary, and then stored in a computer memory. In the context of the present disclosure, a computer-usable or computer-readable, storage medium may be any tangible medium that can contain or store a program for use by or in connection with the instruction execution system, apparatus, or device.

In some implementations, a computer readable signal medium may include a propagated data signal with computer readable program code embodied therein, for example, in baseband or as part of a carrier wave. In some implementations, such a propagated signal may take any of a variety of forms, including, but not limited to, electromagnetic, optical, or any suitable combination thereof. In some implementations, the computer readable program code may be transmitted using any appropriate medium, including but not limited to the internet, wireline, optical fiber cable, RF, etc. In some implementations, a computer readable signal medium may be any computer readable medium that is not a computer readable storage medium and that can communicate, propagate, or transport a program for use by or in connection with an instruction execution system, apparatus, or device.

In some implementations, computer program code for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java®, Smalltalk, C++ or the like. Java® and all Java-based trademarks and logos are trademarks or registered trademarks of Oracle and/or its affiliates. However, the computer program code for carrying out operations of the present disclosure may also be written in conventional procedural programming languages, such as the "C" programming language, PASCAL, or similar programming languages, as well as in scripting languages such as Javascript, PERL, or Python. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN), a wide area network (WAN), a body area network BAN), a personal area network (PAN), a metropolitan area network (MAN), etc., or the connection may be made to an external computer (for example, through the internet using an Internet Service Provider). In some implementations, electronic circuitry including, for example, programmable logic circuitry, an application specific integrated circuit (ASIC), field-programmable gate arrays (FPGAs) or other hardware accelerators, micro-controller units (MCUs), or programmable logic arrays (PLAs) may execute the computer readable program instructions/code by utilizing state information of the computer readable program instructions to personalize the electronic circuitry, in order to perform aspects of the present disclosure.

In some implementations, the flowchart and block diagrams in the figures illustrate the architecture, functionality, and operation of possible implementations of apparatus (systems), methods and computer program products according to various implementations of the present disclosure. Each block in the flowchart and/or block diagrams, and combinations of blocks in the flowchart and/or block diagrams, may represent a module, segment, or portion of code, which comprises one or more executable computer program instructions for implementing the specified logical function(s)/act(s). These computer program instructions may be provided to a processor of a general purpose computer, special purpose computer, or other programmable data processing apparatus to produce a machine, such that the computer program instructions, which may execute via the processor of the computer or other programmable data processing apparatus, create the ability to implement one or more of the functions/acts specified in the flowchart and/or block diagram block or blocks or combinations thereof. It should be noted that, in some implementations, the functions noted in the block(s) may occur out of the order noted in the figures (or combined or omitted). For example, two blocks shown in succession may, in fact, be executed substantially concurrently, or the blocks may sometimes be executed in the reverse order, depending upon the functionality involved.

In some implementations, these computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks or combinations thereof.

In some implementations, the computer program instructions may also be loaded onto a computer or other programmable data processing apparatus to cause a series of operational steps to be performed (not necessarily in a particular order) on the computer or other programmable apparatus to produce a computer implemented process such that the instructions which execute on the computer or other programmable apparatus provide steps for implementing the functions/acts (not necessarily in a particular order) specified in the flowchart and/or block diagram block or blocks or combinations thereof.

Referring now to the example implementation of FIG. 1, there is shown tracking process 10 that may reside on and may be executed by a computer (e.g., computer 12), which may be connected to a network (e.g., network 14) (e.g., the internet or a local area network). Examples of computer 12 (and/or one or more of the client electronic devices noted below) may include, but are not limited to, a storage system (e.g., a Network Attached Storage (NAS) system, a Storage Area Network (SAN)), a personal computer(s), a laptop computer(s), mobile computing device(s), a server computer, a series of server computers, a mainframe computer(s), or a computing cloud(s). A SAN may include one or more of the client electronic devices, including a RAID device and a NAS system. In some implementations, each of the aforementioned may be generally described as a computing device. In certain implementations, a computing device may be a physical or virtual device. In many implementations, a computing device may be any device capable of performing operations, such as a dedicated processor, a portion of a processor, a virtual processor, a portion of a virtual processor, portion of a virtual device, or a virtual device. In some implementations, a processor may be a physical processor or a virtual processor. In some implementations, a virtual processor may correspond to one or more parts of one or more physical processors. In some implementations, the instructions/logic may be distributed and executed across one or more processors, virtual or physical, to execute the instructions/logic. Computer 12 may execute an operating system, for example, but not limited to, Microsoft® Windows®; Mac® OS X®; Red Hat® Linux®, Windows® Mobile, Chrome OS, Blackberry OS, Fire OS, or a custom operating system. (Microsoft and Windows are registered trademarks of Microsoft Corporation in the United States, other countries or both; Mac and OS X are registered trademarks of Apple Inc. in the United States, other countries or both; Red Hat is a registered trademark of Red Hat Corporation in the United States, other countries or both; and Linux is a registered trademark of Linus Torvalds in the United States, other countries or both).

In some implementations, as will be discussed below in greater detail, a tracking process, such as tracking process 10 of FIG. 1, may determine that a user wears a wearable device during one or more time periods. A total amount of time that the user is wearing the wearable device during the one or more time periods may be tracked. The total amount of time that the user wears the wearable device during the one or more time periods may be transmitted to a computing device for display on a user interface.

In some implementations, as will also be discussed below in greater detail, a tracking process, such as tracking process 10 of FIG. 1, may receive, by a computing device, a total amount of time that a user wears a wearable device during one or more time periods. The total amount of time that the user wears the wearable device during the one or more time periods may be compared to a threshold amount of time for the one or more time periods. A remaining amount of time for the user to wear the wearable device during the one or more time periods may be displayed on a user interface based upon, at least in part, comparing the total amount of time that the user wears the wearable device during the one or more time periods to the threshold amount of time.

In some implementations, the instruction sets and subroutines of tracking process 10, which may be stored on storage device, such as storage device 16, coupled to computer 12, may be executed by one or more processors and one or more memory architectures included within computer 12. In some implementations, storage device 16 may include but is not limited to: a hard disk drive; all forms of flash memory storage devices; a tape drive; an optical drive; a RAID array (or other array); a random access memory (RAM); a read-only memory (ROM); or combination thereof. In some implementations, storage device 16 may be organized as an extent, an extent pool, a RAID extent (e.g., an example 4D+1P R5, where the RAID extent may include, e.g., five storage device extents that may be allocated from, e.g., five different storage devices), a mapped RAID (e.g., a collection of RAID extents), or combination thereof.

In some implementations, network 14 may be connected to one or more secondary networks (e.g., network 18), examples of which may include but are not limited to: a local area network; a wide area network or other telecommunications network facility; or an intranet, for example. The phrase "telecommunications network facility," as used herein, may refer to a facility configured to transmit, and/or receive transmissions to/from one or more mobile client electronic devices (e.g., cellphones, etc.) as well as many others.

In some implementations, computer 12 may include a data store 20, such as a database (e.g., relational database, object-oriented database, triplestore database, etc.) and may be located within any suitable memory location, such as storage device 16 coupled to computer 12. In some implementations, data, metadata, information, etc. described throughout the present disclosure may be stored in the data store. In some implementations, computer 12 may utilize any known database management system such as, but not limited to, DB2, in order to provide multi-user access to one or more databases, such as the above noted relational database. In some implementations, the data store may also be a custom database, such as, for example, a flat file database or an XML database. In some implementations, any other form(s) of a data storage structure and/or organization may also be used. In some implementations, tracking process 10 may be a component of the data store, a standalone application that interfaces with the above noted data store and/or an applet/application that is accessed via client applications 22, 24, 26, 28. In some implementations, the above noted data store may be, in whole or in part, distributed in a cloud computing topology. In this way, computer 12 and storage device 16 may refer to multiple devices, which may also be distributed throughout the network.

In some implementations, computer 12 may execute a brace application (e.g., brace application 20), examples of which may include, but are not limited to, e.g., a time tracking application, a calendar application, a sensor recording application, or other application that allows for the tracking and maintaining of information related to a user wearing a back brace (or other medical brace). An example of brace application 20 may be the application provided by BraceTrack, LLC of Fort Lauderdale, Fla. However, it will be appreciated that any application and user interface capable of performing the present disclosure may also be used without departing from the scope of the present disclosure. As such, the application provided by BraceTrack should be taken as example only and not to otherwise limit the scope of the present disclosure.

In some implementations, tracking process 10 and/or brace application 20 may be accessed via one or more of client applications 22, 24, 26, 28. In some implementations, tracking process 10 may be a standalone application, or may be an applet/application/script/extension that may interact with and/or be executed within brace application 20, a component of brace application 20, and/or one or more of client applications 22, 24, 26, 28. In some implementations, brace application 20 may be a standalone application, or may be an applet/application/script/extension that may interact with and/or be executed within tracking process 10, a component of tracking process 10, and/or one or more of client applications 22, 24, 26, 28. In some implementations, one or more of client applications 22, 24, 26, 28 may be a standalone application, or may be an applet/application/script/extension that may interact with and/or be executed within and/or be a component of tracking process 10 and/or brace application 20. Examples of client applications 22, 24, 26, 28 may include, but are not limited to, e.g., a time tracking application, a calendar application, a sensor recording application, or other application that allows for the tracking and maintaining of information related to a user wearing a back brace (or other medical brace), a brace application, a standard and/or mobile web browser, an email application (e.g., an email client application), a textual and/or a graphical user interface, a customized web browser, a plugin, an Application Programming Interface (API), or a custom application. The instruction sets and subroutines of client applications 22, 24, 26, 28, which may be stored on storage devices 30, 32, 34, 36, 30*a*, 32*a*, 34*a*, 36*a*, coupled to client electronic devices 38, 40, 42, 44 and/or brace 64, 66, 68, 70, may be executed by one or more processors and one or more memory architectures incorporated into client electronic devices 38, 40, 42, 44 and/or brace 64, 66, 68, 70**.

In some implementations, one or more of storage devices 30, 32, 34, 36, 30*a*, 32*a*, 34*a*, 36*a*, may include but are not limited to: hard disk drives; flash drives, tape drives; optical drives; RAID arrays; random access memories (RAM); and read-only memories (ROM). Examples of client electronic devices 38, 40, 42, 44 (and/or computer 12) may include, but are not limited to, a personal computer (e.g., client electronic device 38), a laptop computer (e.g., client electronic device 40), a smart/data-enabled, cellular phone (e.g., client electronic device 42), a notebook computer (e.g., client electronic device 44), a tablet, a server, a television, a smart television, a smart speaker, an Internet of Things (IoT) device, a media (e.g., audio/video, photo, etc.) capturing and/or output device, an audio input and/or recording device (e.g., a handheld microphone, a lapel microphone, an embedded microphone (such as those embedded within eyeglasses, smart phones, tablet computers and/or watches, etc.), a brace (e.g., back brace), and a dedicated network device. Additionally/alternatively, one or more of client electronic devices 38, 40, 42, 44 may include (or may be a separate) monitoring device/sensor (e.g., also referred to herein as brace 64, 66, 68, 70). Client electronic devices 38, 40, 42, 44** may each execute an operating system, examples of which may include but are not limited to, Android™, Apple® iOS®, Mac® OS X®; Red Hat® Linux®, Windows® Mobile, Chrome OS, Blackberry OS, Fire OS, or a custom operating system.

In some implementations, one or more of client applications 22, 24, 26, 28 may be configured to effectuate some or all of the functionality of tracking process 10 (and vice versa). Accordingly, in some implementations, tracking process 10 may be a purely server-side application, a purely client-side application, or a hybrid server-side/client-side application that is cooperatively executed by one or more of client applications 22, 24, 26, 28 and/or tracking process 10.

In some implementations, one or more of client applications 22, 24, 26, 28 may be configured to effectuate some or all of the functionality of brace application 20 (and vice versa). Accordingly, in some implementations, brace application 20 may be a purely server-side application, a purely client-side application, or a hybrid server-side/client-side application that is cooperatively executed by one or more of client applications 22, 24, 26, 28 and/or brace application 20. As one or more of client applications 22, 24, 26, 28, tracking process 10, and brace application 20, taken singly or in any combination, may effectuate some or all of the same functionality, any description of effectuating such functionality via one or more of client applications 22, 24, 26, 28, tracking process 10, brace application 20, or combination thereof, and any described interaction(s) between one or more of client applications 22, 24, 26, 28, tracking process 10, brace application 20, or combination thereof to effectuate such functionality, should be taken as an example only and not to limit the scope of the disclosure.

In some implementations, one or more of users 46, 48, 50, 52 and/or one or more of brace 64, 66, 68, 70 may access computer 12 and tracking process 10 (e.g., using one or more of client electronic devices 38, 40, 42, 44) directly through network 14 or through secondary network 18. Further, computer 12 may be connected to network 14 through secondary network 18, as illustrated with phantom link line 54. Tracking process 10 may include one or more user interfaces, such as browsers and textual or graphical user interfaces, through which users 46, 48, 50, 52 may access tracking process 10 and/or brace 64, 66, 68, 70.

In some implementations, one or more of the various client electronic devices and/or one or more of brace 64, 66, 68, 70 may be directly or indirectly coupled to network 14 (or network 18). For example, personal computer 38 and brace 64 are shown directly coupled to network 14 via a hardwired network connection. Further, notebook computer 44 and brace 70 are shown directly coupled to network 18 via a hardwired network connection. Laptop computer 40 and brace 66 are shown wirelessly coupled to network 14 via wireless communication channels 56a and 56b respectively established between laptop computer 40 and wireless access point (i.e., WAP) 58 and between brace 66 and WAP 58, which is shown directly coupled to network 14. WAP 58 may be, for example, an IEEE 802.11a, 802.11b, 802.11g, Wi-Fi®, RFID, and/or Bluetooth™ (including Bluetooth™ Low Energy) device that is capable of establishing wireless communication channel 56a between laptop computer 40 and WAP 58 and wireless communication channel 56b between brace 66 and WAP 58. Additionally/alternatively, a brace (e.g., brace 66) may be directly (and/or wirelessly) coupled to a client electronic device (e.g., client electronic device 40) as illustrated with phantom link line 55. Thus, information may be communicated from a brace (e.g., brace 66) to a client electronic device (e.g., client electronic device 40), where the information may be communicated, e.g., to computer 12 via, e.g., a network (e.g., network 14). Smart phone 42 and brace 68 are shown wirelessly coupled to network 14 via wireless communication channels 60a and 60b respectively established between smart phone 42 and cellular network/bridge 62 and brace 68 and cellular network/bridge 62, which is shown by example directly coupled to network 14.

In some implementations, some or all of the IEEE 802.11x specifications may use Ethernet protocol and carrier sense multiple access with collision avoidance (i.e., CSMA/CA) for path sharing. The various 802.11x specifications may use phase-shift keying (i.e., PSK) modulation or complementary code keying (i.e., CCK) modulation, for example. Bluetooth™ (including Bluetooth™ Low Energy) is a telecommunications industry specification that allows, e.g., mobile phones, computers, smart phones, and other electronic devices (e.g., brace 64, 66, 68, 70) to be interconnected using a short-range wireless connection. Other forms of interconnection (e.g., Near Field Communication (NFC)) may also be used.

In some implementations, various I/O requests (e.g., I/O request 15) may be sent from, e.g., client applications 22, 24, 26, 28 and/or brace 64, 66, 68, 70 to, e.g., computer 12 (and vice versa). Examples of I/O request 15 may include but are not limited to, data write requests (e.g., a request that content be written to computer 12) and data read requests (e.g., a request that content be read from computer 12). Other examples of I/O request 15 may include sensor data transmitted between the brace and computer 12, or other type of data indicating that a user is wearing the brace.

Figure 2:
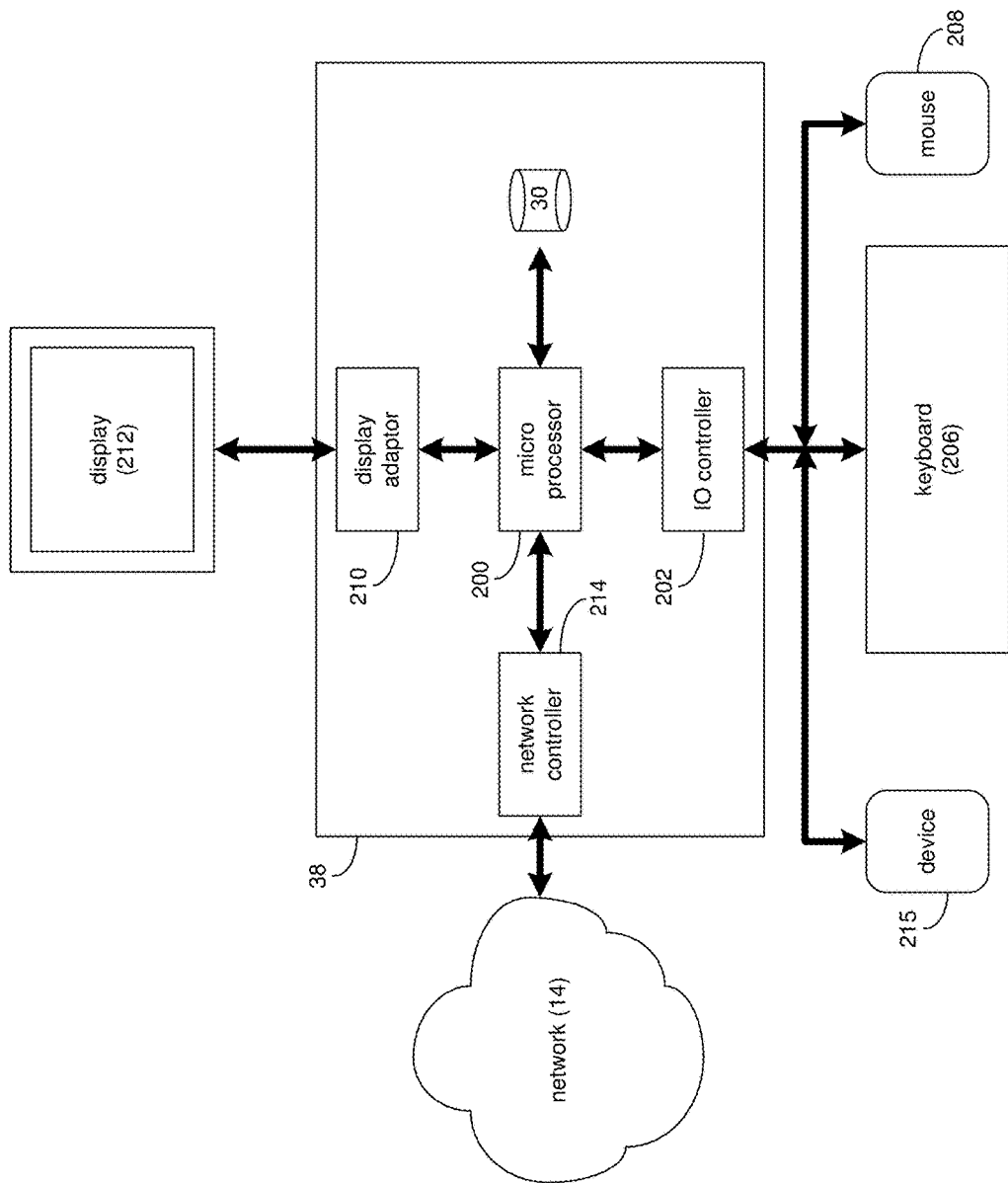
FIG. 2 is an example diagrammatic view of a client electronic device of FIG. 1 according to one or more example implementations of the disclosure.

Referring also to the example implementation of FIG. 2, there is shown a diagrammatic view of client electronic device 38. While client electronic device 38 is shown in this figure, this is for example purposes only and is not intended to be a limitation of this disclosure, as other configurations are possible. Additionally, any computing device capable of executing, in whole or in part, tracking process 10 may be substituted for client electronic device 38 (in whole or in part) within FIG. 2, examples of which may include but are not limited to computer 12 and/or one or more of client electronic devices 38, 40, 42, 44 and/or one or more of brace 64, 66, 68, 70.

In some implementations, client electronic device 38 may include a processor (e.g., microprocessor 200) configured to, e.g., process data and execute the above-noted code/instruction sets and subroutines. Microprocessor 200 may be coupled via a storage adaptor to the above-noted storage device(s) (e.g., storage device 30). An I/O controller (e.g., I/O controller 202) may be configured to couple microprocessor 200 with various devices (e.g., via wired or wireless connection), such as keyboard 206, pointing/selecting device (e.g., touchpad, touchscreen, mouse 208, etc.), custom device (e.g., device 215 such as a sensor), USB ports, and printer ports. A display adaptor (e.g., display adaptor 210) may be configured to couple display 212 (e.g., touchscreen monitor(s), plasma, CRT, or LCD monitor(s), etc.) with microprocessor 200, while network controller/adaptor 214 (e.g., an Ethernet adaptor) may be configured to couple microprocessor 200 to the above-noted network 14 (e.g., the Internet or a local area network).

Generally, after a patient is diagnosed with a back problem (e.g., idiopathic scoliosis), a doctor or other health processional may prescribe a back brace. In order for it to significantly improve the position of the spine, guidelines say the brace has to be worn a certain number of hours per day based on the patient's spinal curvature (commonly up to or exceeding eighteen hours a day). Patients must adhere to these guidelines to reap the full benefits of the back brace. It is generally difficult to keep track of the hours that the patient wears the brace. Therefore, as will be discussed below, to help patients and doctors easily, accurately, efficiently, and verifiably track the time and "banked time" the brace is worn, the present disclosure may include a sensor that may be separate from a back brace, or included in the back brace, that may track how long a user is wearing the brace. As will also be discussed below, the present disclosure may include an application that may maintain an accurate log of how long the user is wearing the brace (e.g., either by manual entry by the user or automatically by receiving data from the brace sensor) which may be displayed to the user.

As will be discussed below, tracking process 10 may at least help, e.g., improve existing technological processes, necessarily rooted in computer technology in order to overcome an example and non-limiting problem specifically arising in the realm of patient adherence to wearing a brace, and being integrated into the practical application of monitoring and tracking such an adherence automatically and/or manually. It will be appreciated that the computer processes described throughout are integrated into one or more practical applications, and when taken at least as a whole are not considered to be well-understood, routine, and conventional functions.

The Tracking Process:

As discussed above and referring also at least to the example implementations of FIGS. 3-8, tracking process 10 may determine 300 that a user wears a wearable device during one or more time periods. Tracking process 10 may track 302 a total amount of time that the user is wearing the wearable device during the one or more time periods. Tracking process 10 may transmit 304 the total amount of time that the user wears the wearable device during the one or more time periods to a computing device for display on a user interface.

As noted above, after a patient is diagnosed with a back problem (e.g., idiopathic scoliosis), a doctor or other health processional may prescribe a back brace to be worn by the patient. In order for it to significantly improve the position of the spine, guidelines say the brace has to be worn a certain number of hours per day based on the patient's spinal curvature (commonly at least eighteen hours a day but other times/guidelines may be used). Patients must typically adhere to these guidelines to reap the full benefits of the back brace, which may be onerous to track.

Figure 5:
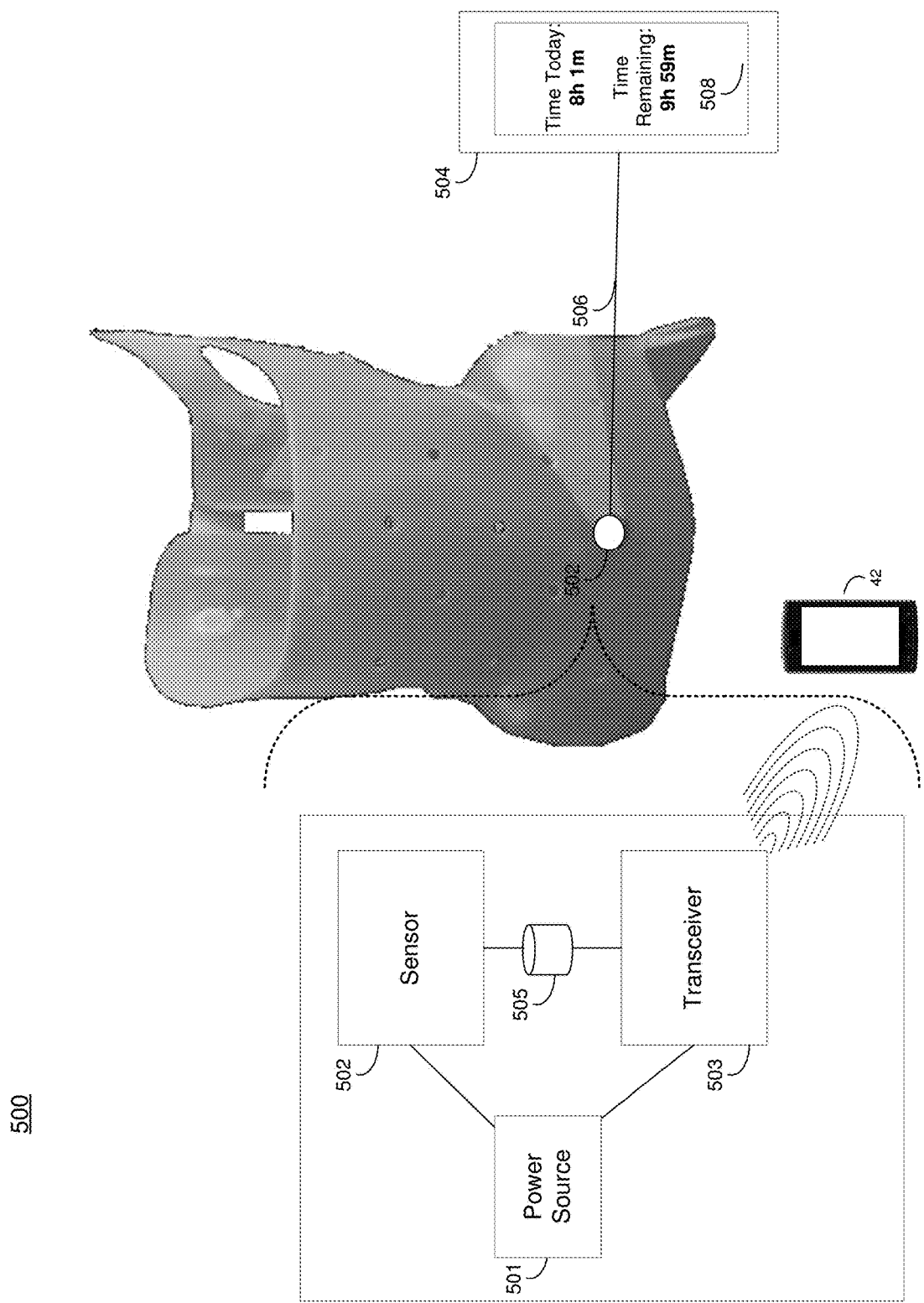
FIG. 5 is an example diagrammatic view of a back brace according to one or more example implementations of the disclosure.

As such, in some implementations, tracking process 10 may determine 300 that a user wears a wearable device during one or more time periods. For instance, and referring at least to the example implementation of FIG. 5, an example wearable device (e.g., back brace 500) is shown. As used herein, the terms wearable device, back brace, and brace may be used interchangeably. As shown in FIG. 5 and discussed further below, back brace 500 may include at least one sensor (e.g., sensor 502), a power source 501 (e.g., battery or direct AC connection), a transceiver 503 (e.g., Bluetooth Low Energy (BLE) System on Chip (SOC) transceiver), and memory 505.

For example, in some implementations, a sensor connected to the wearable device (e.g., back brace 500) may determine 300 that the user wears (or is wearing) the wearable device during one or more time periods. For instance, as shown in FIG. 5, at least one sensor (e.g., sensor 502) may be attached to or embedded within back brace 500. For example, in a common back brace, sensor 502 may be located in the front of back brace 500 (e.g., approximating the position of the user's belly button) and may be of a thickness typical of back brace 500 or any other thickness capable of operating effectively. In some implementations, sensor 502 may include at least one of a capacitive sensor, a proximity sensor, a pressure sensor, a temperature sensor, and a motion sensor. For example, when sensor 502 is a pressure sensor, the pressure sensor may be positioned anywhere on the inside of back brace 500 so as to be pressed (or sense sufficient pressure) when back brace 500 is worn. In the example, when wearing back brace 500, the user would inherently apply sufficient pressure or "press" upon the sensor with the user's body to provide an indication signal to make a determination 300 that back brace 500 is being worn. As another example, when sensor 502 is a temperature sensor, the temperature sensor may be positioned anywhere on the inside of back brace 500 so as to detect temperature when back brace 500 is worn. In the example, when wearing back brace 500, the user would cover sensor 502, thereby changing the current temperature detected by sensor 502. In some implementations, sensor 502 may be based on a dual channel capacitive proximity sensor (e.g., detects the presence or absence of virtually any object, such as the user wearing brace 500, regardless of material by utilizing the electrical property of capacitance and the change of capacitance based on a change in the electrical field around the active face of the sensor), as well as a proximity sensor (e.g., detecting the presence or absence of an object, such as the user wearing brace 500, using electromagnetic fields, light, and sound) which may be used to detect the wear state of the brace for a long period of time, or combination conductance proximity sensor. Temperature sensing may be used to account for drift in capacitance due to temperature changes. A non-limiting example of such a sensor is the AZD107 or IQS620/IQS620A sensor offered by Azoteq of Austin Tex. In some implementations, when temperature is detected within a certain range (e.g., between 96 and 102 degrees) this would provide an indication signal to make a determination 300 that back brace 500 is being worn. As yet another example, when sensor 502 is a motion/movement sensor (e.g., accelerometer, gyroscope, GPS, etc.), this sensor may be positioned anywhere on the inside and/or outside of back brace 500 so as to detect movement when back brace 500 is worn. In the example, when wearing back brace 500, the user may move around, causing sensor 502 to detect this movement to provide an indication signal to make a determination 300 that back brace 500 is being worn.

In some implementations, to help increase accuracy, any combination and any number of the above-noted sensors may be used. For instance, only one sensor (e.g., temperature) determining that back brace 500 is being worn may not be sufficient to make a final determination that back brace 500 is being worn (e.g., if it is already warm in the room or the brace is in the sunlight), whereas two or more sensors (e.g., temperature and pressure) essentially simultaneously determining that back brace 500 is being worn may be sufficient to make a final determination that back brace 500 is being worn. As another example, only one pressure sensor determining that back brace 500 is being worn may not be sufficient to make a final determination that back brace 500 is being worn (e.g., if something is accidentally resting on top of the pressure sensor), whereas two or more pressure sensors determining that back brace 500 is being worn may be sufficient to make a final determination that back brace 500 is being worn.

In some implementations, tracking process 10 may track 302 (e.g., monitor) a total amount of time that the user is wearing the wearable device during the one or more time periods. For instance, in some implementations, the on/off state of any of the above sensors may be captured over, e.g., I²C with a Bluetooth Low Energy (BLE) System on Chip (SOC) (e.g., via transceiver 503) or Wi-Fi, etc. The BLE SOC may contain a radio to connect with a computing device (e.g., mobile phone/tablet, etc. and/or a microprocessor) to process the data stream from the sensor. The module may also contain memory 505 (e.g., flash memory) to temporarily store sensor readings along with a timestamp. Sensor data may be temporarily stored in the module for situations where the receiving mobile device is either not within transmission proximity of the sensor or is turned off. The BLE module may advertise its presence continuously or periodically. The computing device may pick up those advertising signals and connect to sensor 502 using, e.g., Bluetooth Low Energy. Once a connection is established, the computing device may request on/off events along with the timestamp from sensor 502.

In some implementations, using the above-noted sensor(s) 502 to determine whether or not the user is wearing back brace 500, tracking process 10 may (e.g., using the above-noted timestamp or otherwise) track 302 (e.g., monitor) how long the user is wearing back brace 500 for a particular time period (e.g., one day, one week, one month, etc.). For example, assume that sensor 502 is used to determine that the user is wearing back brace 500 for 8 hours on Monday (e.g., 4 hours from 10 am to 2 pm and then 4 hours from 4 pm to 8 pm). In the example, tracking process 10 may track 302 that the user has worn back brace 500 for 8 hours on Monday. As another example, assume that sensor 502 is used to determine that the user is wearing back brace 500 for 8 hours on Monday, and 6 hours on Tuesday of the same week. In the example, tracking process 10 may track 302 that the user has worn back brace 500 for 8 hours on Monday and 6 hours on Tuesday of the same week.

In some implementations, tracking process 10 may transmit 304 the total amount of time that the user wears the wearable device during the one or more time periods to a computing device for display on a user interface. For example, as will be discussed in greater detail below, the total amount of time where the user was determined to have worn back brace 500 (e.g., 8 hours on Monday and/or 6 hours on Tuesday) may be transmitted 304 to a computing device (e.g., client electronic device 42 via client application 26 and/or to computer 12 which may then be transmitted to client electronic device 42) to log and display this amount of time for the user (or medical professional) on a user interface (e.g., user interface 508). In some implementations, the data may be transmitted 304 wirelessly (as discussed above) and/or the data may be transmitted 304 via a wired connection (as discussed above). While client electronic device 42 may be a mobile device (e.g., smart phone), in some implementations, the client electronic device may be a wired device that is wired directly to sensor 502. For instance, as shown in FIG. 5, client electronic device 504 is shown connected to back brace 500 via wired connection 506. Client electronic device 504 may include a user interface capable of displaying the above-noted amount of time back brace 500 is worn or time remaining to be worn, or any other relevant information, such as those discussed below with FIGS. 6-8.

In some implementations, the total amount of time that the user wears the wearable device during the one or more time periods may be transmitted 304 automatically. For example, as will be discussed further below, the total amount of time that the user wears back brace 500 may be transmitted in real-time (e.g., in example intervals of 1-2 seconds or minutes) as the user is wearing back brace 500. In some implementations, the total amount of time that the user wears back brace 500 may be transmitted after sensor 502 determines that the user is no longer wearing back brace 500, which may help save resources (e.g., battery life, processing resources, storage space, bandwidth, etc.) of back brace 500 and/or client electronic device 42. In some implementations, the total amount of time may be verified by the user prior to transmitting and/or after transmitting.

In some implementations, the total amount of time that the user wears the wearable device during the one or more time periods may be transmitted 304 manually. For example, as will be discussed further below, the total amount of time that the user wears back brace 500 may be transmitted manually. For instance, the user may manually upload and/or enter the hours/minutes into client electronic device 42 via a user interface of client application 26. In some implementations, manual entry need not require use of sensor 502, and client electronic device 504 may include a timer that the user may be manually started and stopped by the user to determine how long back brace 500 has been worn. In some implementations, manual entry may still use sensor 502, where client electronic device 504 may include a timer that may start and stop depending on the use of the sensor to determine whether back brace 500 is being worn, which may be verified by the user and then added manually (or added automatically without verification).

Additionally, as also discussed above and referring also at least to the example implementations of FIGS. 4-8, tracking process 10 may receive 400, by a computing device, a total amount of time that a user wears a wearable device during one or more time periods. Tracking process 10 may compare 402 the total amount of time that the user wears the wearable device during the one or more time periods to a threshold amount of time for the one or more time periods. Tracking process 10 may display 404 on a user interface a remaining amount of time for the user to wear the wearable device during the one or more time periods based upon, at least in part, comparing the total amount of time that the user wears the wearable device during the one or more time periods to the threshold amount of time.

In some implementations, tracking process 10 may receive 400, by a computing device, a total amount of time that a user wears a wearable device during one or more time periods. For instance, one or more implementations of the above-described back brace 500 may be used to transmit the above-noted total amount of time that the user wears back brace 500, which may be received 400 by tracking process 10 (e.g., via sensor 502 connected to the wearable device, wherein the sensor may include at least one of a pressure sensor, a temperature sensor, and a motion sensor). As described above, the total amount of time where the user was determined to have worn back brace 500 (e.g., 8 hours on Monday and/or 6 hours on Tuesday) may be transmitted 304 to and received 400 by a computing device (e.g., client electronic device 42 via client application 26 and/or to computer 12 which may then be transmitted to and received 400 by client electronic device 42) to log and display for the user (or medical professional) on a user interface this amount of time (discussed below).

As also noted above, the total amount of time that the user wears the wearable device during the one or more time periods may be received 400 automatically, and in some implementations the total amount of time that the user wears the wearable device during the one or more time periods may be received 400 manually. For instance, and referring at least to the example implementation of FIG. 6, an example user interface 600 (e.g., of tracking process 10 via client application 26 of client electronic device 42) is shown. In the example, an "Add Time" icon 602 may be selected by the user using any known technique (e.g., touch screen). By selecting this example icon 602, the user may manually upload and/or enter the hours/minutes into client electronic device 42 via user interface 600 of client application 26. In some implementations, manual entry need not require use of sensor 502, and client electronic device 504 may include a timer that the user may manually start (e.g., via icon 604) and stop (e.g., via icon 606) to determine how long back brace 500 has been worn (e.g., for the current day). In some implementations, manual entry may still use sensor 502, where client electronic device 504 may include a timer that may start and stop depending on the use of the sensor to determine whether back brace 500 is being worn, which may be verified by the user and then added manually (or added automatically without verification).

Figure 6:
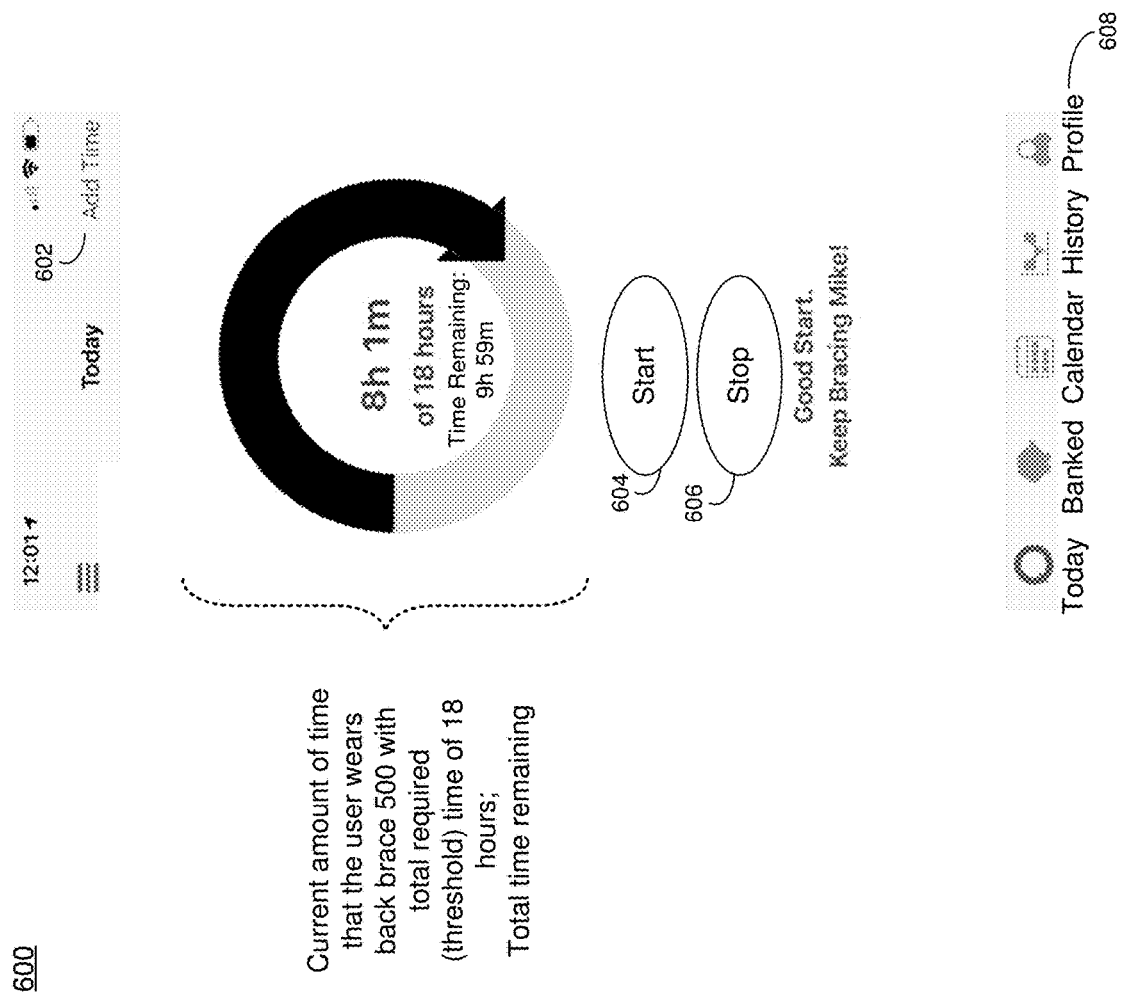
FIG. 6 is an example diagrammatic view of a user interface displayed by a tracking process according to one or more example implementations of the disclosure.

In some implementations, tracking process 10 may compare 402 the total amount of time that the user wears the wearable device during the one or more time periods to a threshold amount of time for the one or more time periods, and in some implementations, tracking process 10 may display 404 on a user interface a remaining amount of time for the user to wear the wearable device during the one or more time periods based upon, at least in part, comparing the total amount of time that the user wears the wearable device during the one or more time periods to the threshold amount of time. For instance, assume for example purposes only that the user is required to wear back brace 500 for 18 hours (as shown in FIG. 6). In the example, further assume that the user, for the current day, has worn back brace 500 for 8 hours and 1 minute (as also shown in FIG. 6). Tracking process 10 may compare 402 that total amount of time (8 hours and 1 minute) to the required (threshold) amount of time for that same day (18 hours). As a result, tracking process 10 may display 404 (e.g., via user interface 600) the remaining amount of time that the user should wear back brace 500 (e.g., 9 hours and 59 minutes) to meet the above-noted guidelines. In some implementations, the threshold amount of time may be changed in the user's profile (e.g., via profile icon 608), which may include other options as well (e.g., entering the user's name, device pairing options or other connectivity options, etc.).

Figure 7:
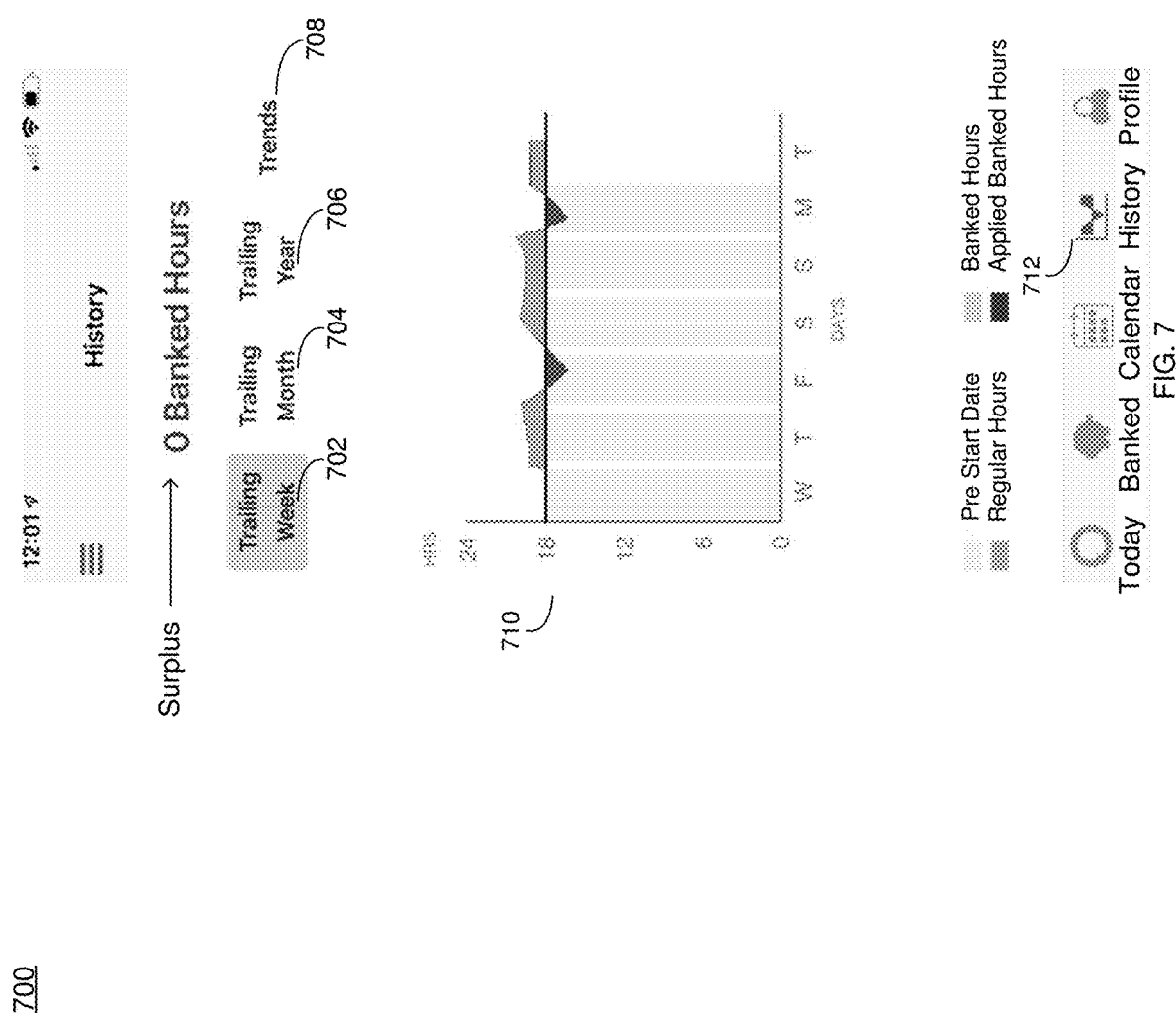
FIG. 7 is an example diagrammatic view of a user interface displayed by a tracking process according to one or more example implementations of the disclosure.

In some implementations, displaying 404 on the user interface the remaining amount of time for the user to wear the wearable device during the one or more time periods may include displaying 406 a surplus amount of time above the threshold amount of time that the user wears the wearable device during the one or more time periods. For instance, and referring to the example implementation of FIG. 7, an example user interface (e.g., user interface 700 of tracking process 10 via client application 26 of client electronic device 42) is shown. In the example, tracking process 10 may display 406 a surplus amount of time that is above the threshold amount of time that the user is required to wear back brace 500. For instance, and continuing with the above example, assume for example purposes only that the threshold amount of time for a particular period (e.g., a single day) is 18 hours, and further assume that tracking process 10 has only received data indicating that the user has worn back brace 500 for 8 hours and 1 minute for that same day. In the example, there would be 0 surplus or "banked" hours (as shown in FIG. 7), as the user has not even worn back brace 500 long enough to meet the threshold of 18 hours, let alone worn back brace 500 longer than the threshold of 18 hours. However, now assume that tracking process 10 has received data indicating that the user has worn back brace 500 for 19 hours and 1 minute for that same day. In the example, there would be 1 hour and 1 minute surplus or "banked" hours shown in FIG. 7, as the user has worn back brace 500 for 1 hour and 1 minute longer than the threshold of 18 hours. In some implementations, selecting the example "history" icon 712 may display the surplus amount of time, as well as other historical usage data (e.g., history for any given date in the user's brace tracking history). In some implementations, user interface 700 may enable the user to export the user's history of brace time worn and banked for, e.g., the trailing week, month, and year along with daypart trends (e.g., via a PDF (or other format) email, text, etc.) Daypart trends may include, e.g., the typical hours the brace is being worn so the user may visualize patterns by time of day.

It will be appreciated that while the surplus hours is displayed for a particular day, other time periods may also be used when displaying 406 the surplus. For example, now assume that tracking process 10 has received data indicating that the user has worn back brace 500 for 127 hours and 1 minute for the week. In the example, there would be 1 hour and 1 minute surplus or "banked" hours, as the user has worn back brace 500 for 1 hour and 1 minute longer than the threshold of 126 hours for the week (i.e., 18 hours a day×7 days=126 hours). Other time periods that may be used include months, years, etc., which may be viewed in user interface 700 by selecting the appropriate icon (e.g., Trailing week icon 702, Trailing month icon 704, Trailing year icon 706, Trends icon 708, etc., which may be viewed in any form, such as the graph 710, and which may also show the deficit amount of time needed to wear back brace 500 to meet the threshold). As such, the use of a single day as the time period should be taken as example only and not to otherwise limit the scope of the present disclosure.

Figure 8:
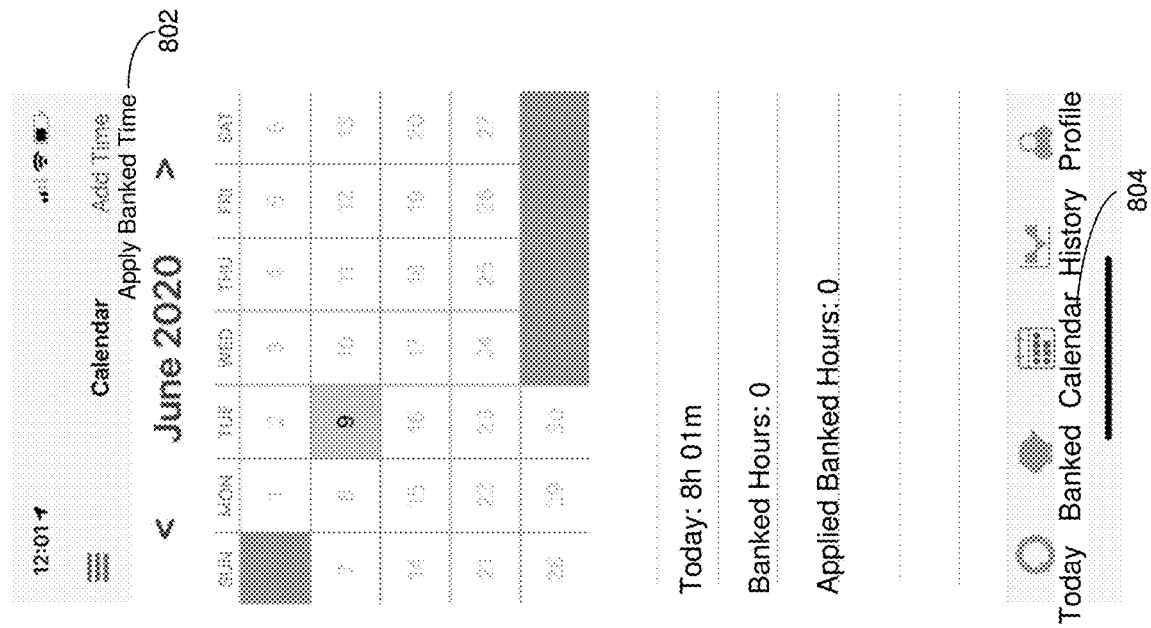
FIG. 8 is an example diagrammatic view of a user interface displayed by a tracking process according to one or more example implementations of the disclosure.

In some implementations, and referring to the example implementation of FIG. 8, an example user interface (e.g., user interface 800 of tracking process 10 via client application 26 of client electronic device 42) is shown. In the example, information pertaining to the total amount of time the user has worn back brace 500 may be displayed by tacking process 10 and viewed by the user in calendar form (e.g., by selecting the example "calendar" icon 804). For instance, the user may select the current day (e.g., 9 Jun. 2020), which may display the current information for that day (e.g., 8 hours and 1 minute having worn back brace 500), how many surplus hours have been banked for that day, as well as how many surplus hours have been applied (as will be discussed further below). In some implementations, tracking process 10 may display all available data up to the selected day (e.g., 1 Jun. 2020-9 Jun. 2020), and in other implementations, the user may manually select which days (or months, years, etc.) to include when displaying the available data.

In some implementations, displaying 404 on the user interface the remaining amount of time for the user to wear the wearable device during the one or more time periods may include applying 408 the surplus amount of time above the threshold amount of time to the remaining amount of time for the user to wear the wearable device during the one or more time periods. For instance, assume that tracking process 10 has received data indicating that the user has worn back brace 500 for 19 hours and 1 minute for a particular day (e.g., 8 Jun. 2020). In the example, there would be 1 hour and 1 minute surplus or "banked" hours shown in FIG. 7, as the user has worn back brace 500 for 1 hour and 1 minute longer than the threshold of 18 hours. Now assume that tracking process 10 had also received data indicating that the user has worn back brace 500 for 17 hours and 1 minute for the prior day (e.g., 7 Jun. 2020), leaving a 59 minute deficiency for that prior day. In the example, tracking process 10 may apply 408 the surplus (or "banked") time of 59 minutes from 8 Jun. 2020 to the 59 minute deficiency of 7 Jun. 2020, resulting in the user meeting the 18 hour quota each day for two days.

In the example, the total amount of banked time that has been applied may be displayed on any of the example user interfaces described above. In some implementations, the total amount of banked time that has been applied may be applied automatically by tracking process 10 and/or may be applied manually by tracking process 10 receiving an input from the user (e.g., via example "Apply Banked Time" icon 802) to specifically apply any portion of banked time to any particular day, week, month, etc.

While the description below describes a wearable device as a back brace, it will be appreciated that the wearable device may include other types of wearable devices without departing from the scope of the present disclosure. For example, while in some implementations, the wearable device may be a back brace, in some implementations, the wearable device may include at least one of a knee brace (e.g., for MCL/ACL injuries and for preventive knee braces used commonly in football and contact sports), an ankle brace, a sling (e.g., hamstring or shoulder sling), a removable cast, a posture device, a post-surgical stabilization device, or any other type of wearable device. As such, the use of a back brace should be taken as example only and not to otherwise limit the scope of the present disclosure.

Figure 3:
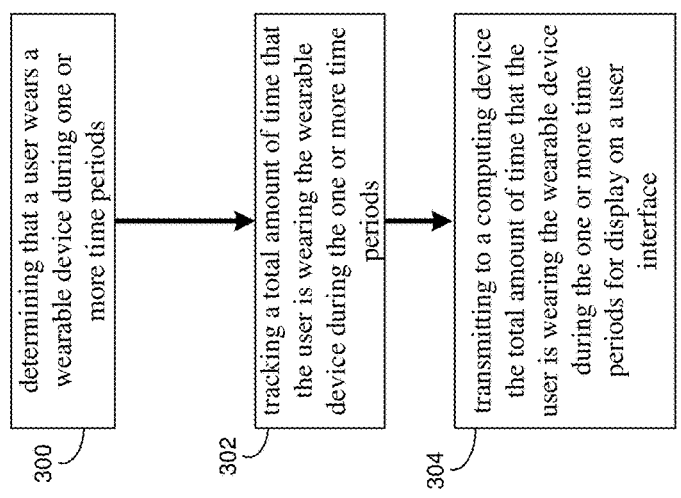
FIG. 3 is an example flowchart of a tracking process according to one or more example implementations of the disclosure.
Figure 4:
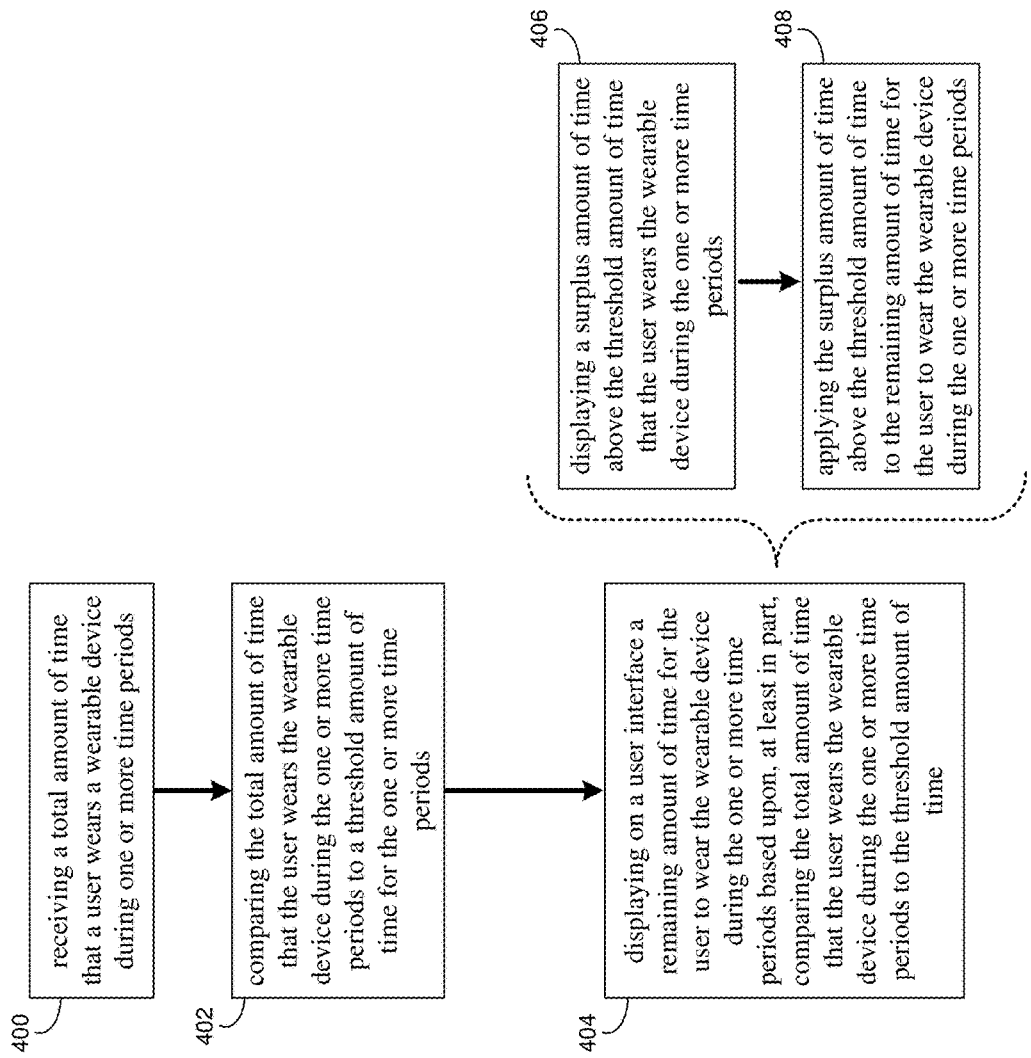
FIG. 4 is an example flowchart of a tracking process according to one or more example implementations of the disclosure

It will be appreciated that tracking process 10, as shown in FIGS. 3 and 4 and also discussed throughout, may be used separately or combined in any combination (e.g., as a brace to collect data, as an application to culminate and display the data, as a brace to collect data that then transmits the data to the application to culminate and display the data, or a single apparatus capable of collecting and culminating data for display, etc.). As such, the use of a separate device (e.g., brace with sensor) and a separate application should be taken as example only and not to otherwise limit the scope of the present disclosure.

The terminology used herein is for the purpose of describing particular implementations only and is not intended to be limiting of the disclosure. As used herein, the singular forms "a", "an" and "the" are intended to include the plural forms as well, unless the context clearly indicates otherwise. As used herein, the language "at least one of A, B, and C" (and the like) should be interpreted as covering only A, only B, only C, or any combination of the three, unless the context clearly indicates otherwise. It will be further understood that the terms "comprises" and/or "comprising," when used in this specification, specify the presence of stated features, integers, steps (not necessarily in a particular order), operations, elements, and/or components, but do not preclude the presence or addition of one or more other features, integers, steps (not necessarily in a particular order), operations, elements, components, and/or groups thereof.

The corresponding structures, materials, acts, and equivalents (e.g., of all means or step plus function elements) that may be in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications, variations, substitutions, and any combinations thereof will be apparent to those of ordinary skill in the art without departing from the scope and spirit of the disclosure. The implementation(s) were chosen and described in order to explain the principles of the disclosure and the practical application, and to enable others of ordinary skill in the art to understand the disclosure for various implementation(s) with various modifications and/or any combinations of implementation(s) as are suited to the particular use contemplated.

Having thus described the disclosure of the present application in detail and by reference to implementation(s) thereof, it will be apparent that modifications, variations, and any combinations of implementation(s) (including any modifications, variations, substitutions, and combinations thereof) are possible without departing from the scope of the disclosure defined in the appended claims.

What is claimed is:

1. A computer-implemented method comprising:
    receiving, by a computing device, a total amount of time that a user wears a wearable device during a plurality of time periods of equal duration;
    comparing the total amount of time that the user wears the wearable device during each of the plurality of one or more time periods to a threshold amount of time for each of the plurality of time periods; and
    displaying on a user interface a remaining amount of time for the user to wear the wearable device during each of the plurality of time periods based upon, at least in part, comparing the total amount of time that the user wears the wearable device during each of the plurality of time periods to the threshold amount of time for each of the plurality of time periods, wherein displaying on the user interface the remaining amount of time for the user to wear the wearable device during each of the plurality of time periods includes displaying a surplus amount of time above the threshold amount of time for each of the plurality of time periods that the user wears the wearable device during each of the plurality of time periods, and wherein displaying on the user interface the remaining amount of time for the user to wear the wearable device during each of the plurality of time periods further includes applying at least a portion of the surplus amount of time above the threshold amount of time for each of the plurality of time periods to the remaining amount of time for the user to wear the wearable device during each of the plurality of time periods, wherein applying at least the portion of the surplus amount of time to the remaining amount of time includes:
    receiving a selection from the user of a past time period of the plurality of time periods that the user wore the wearable device below the threshold amount of time, and
    applying at least the portion of the surplus amount of time to the past time period based upon, at least in part, receiving the selection from the user of the past time period.

2. The computer-implemented method of claim 1 wherein the total amount of time that the user wears the wearable device during each of the plurality of time periods is received manually.

3. The computer-implemented method of claim 1 wherein the total amount of time that the user wears the wearable device during each of the plurality of time periods is received automatically.

4. The computer-implemented method of claim 1 wherein the total amount of time that the user wears the wearable device during each of the plurality of time periods is received by a sensor connected to the wearable device, wherein the sensor includes at least one of a capacitive sensor, a proximity sensor, a pressure sensor, a temperature sensor, and a motion sensor.

5. The computer-implemented method of claim 1 wherein the wearable device includes at least one of a back brace, a knee brace, an ankle brace, a sling, a removable cast, a posture device, and a post-surgical stabilization device.

6. A computer program product residing on a computer readable storage medium having a plurality of instructions stored thereon which, when executed across one or more processors, causes at least a portion of the one or more processors to perform operations comprising:
    receiving a total amount of time that a user wears a wearable device during a plurality of time periods of equal duration;
    comparing the total amount of time that the user wears the wearable device during each of the plurality of time periods to a threshold amount of time for each of the plurality of time periods; and
    displaying on a user interface a remaining amount of time for the user to wear the wearable device during each of the plurality of time periods based upon, at least in part, comparing the total amount of time that the user wears the wearable device during each of the plurality of time periods to the threshold amount of time for each of the plurality of time periods, wherein displaying on the user interface the remaining amount of time for the user to wear the wearable device during each of the plurality of time periods includes displaying a surplus amount of time above the threshold amount of time for each of the plurality of time periods that the user wears the wearable device during each of the plurality of time periods, and wherein displaying on the user interface the remaining amount of time for the user to wear the wearable device during each of the plurality of time periods further includes applying at least a portion of the surplus amount of time above the threshold amount of time for each of the plurality of time periods to the remaining amount of time for the user to wear the wearable device during each of the plurality of time periods, wherein applying at least the portion of the surplus amount of time to the remaining amount of time includes:
- receiving a selection from the user of a past time period of the plurality of time periods that the user wore the wearable device below the threshold amount of time, and
- applying at least the portion of the surplus amount of time to the past time period based upon, at least in part, receiving the selection from the user of the past time period.

7. The computer program product of claim 6 wherein the total amount of time that the user wears the wearable device during each of the plurality of time periods is received manually.

8. The computer program product of claim 6 wherein the total amount of time that the user wears the wearable device during each of the plurality of time periods is received automatically.

9. The computer program product of claim 6 wherein the total amount of time that the user wears the wearable device during each of the plurality of time periods is received by a sensor connected to the wearable device, wherein the sensor includes at least one of a capacitive sensor, a proximity sensor, a pressure sensor, a temperature sensor, and a motion sensor.

10. The computer program product of claim 6 wherein the wearable device includes at least one of a back brace, a knee brace, an ankle brace, a sling, a removable cast, a posture device, and a post-surgical stabilization device.

11. A computing system including one or more processors and one or more memories configured to perform operations comprising:
- receiving a total amount of time that a user wears a wearable device during a plurality of time periods of equal duration;
- comparing the total amount of time that the user wears the wearable device during each of the plurality of time periods to a threshold amount of time for each of the plurality of time periods; and
- displaying on a user interface a remaining amount of time for the user to wear the wearable device during each of the plurality of time periods based upon, at least in part, comparing the total amount of time that the user wears the wearable device during each of the plurality of time periods to the threshold amount of time for each of the plurality of time periods, wherein displaying on the user interface the remaining amount of time for the user to wear the wearable device during each of the plurality of time periods includes displaying a surplus amount of time above the threshold amount of time for each of the plurality of time periods that the user wears the wearable device during each of the plurality of time periods, and wherein displaying on the user interface the remaining amount of time for the user to wear the wearable device during each of the plurality of time periods further includes applying at least a portion of the surplus amount of time above the threshold amount of time for each of the plurality of time periods to the remaining amount of time for the user to wear the wearable device during each of the plurality of time periods, wherein applying at least the portion of the surplus amount of time to the remaining amount of time includes:
  - receiving a selection from the user of a past time period of the plurality of time periods that the user wore the wearable device below the threshold amount of time, and
  - applying at least the portion of the surplus amount of time to the past time period based upon, at least in part, receiving the selection from the user of the past time period.

12. The computing system of claim 11 wherein the total amount of time that the user wears the wearable device during each of the plurality of time periods is received manually.

13. The computing system of claim 11 wherein the total amount of time that the user wears the wearable device during each of the plurality of time periods is received automatically.

14. The computing system of claim 11 wherein the total amount of time that the user wears the wearable device during each of the plurality of time periods is received by a sensor connected to the wearable device, wherein the sensor includes at least one of a capacitive sensor, a proximity sensor, a pressure sensor, a temperature sensor, and a motion sensor.

15. The computing system of claim 11 wherein the wearable device includes at least one of a back brace, a knee brace, an ankle brace, a sling, a removable cast, a posture device, and a post-surgical stabilization device.

* * * * *